United States Patent
Calleri

(10) Patent No.: US 8,499,614 B2
(45) Date of Patent: Aug. 6, 2013

(54) FIELD GAS CHROMATOGRAPH WITH FLAME IONIZATION

(75) Inventor: Antonio Calleri, Milan (IT)

(73) Assignee: Geolog S.r.l., Via Della Moscova, Milan (IT)

( * ) Notice: Subject to any disclaimer, the term of this patent is extended or adjusted under 35 U.S.C. 154(b) by 261 days.

(21) Appl. No.: 13/021,460

(22) Filed: Feb. 4, 2011

(65) Prior Publication Data
US 2011/0192214 A1 Aug. 11, 2011

(51) Int. Cl.
*G01N 30/68* (2006.01)

(52) U.S. Cl.
USPC ........................... 73/23.38; 422/54

(58) Field of Classification Search
USPC ............................. 73/23.35, 23.38
See application file for complete search history.

(56) References Cited

U.S. PATENT DOCUMENTS

| | | | |
|---|---|---|---|
| 5,741,711 A * | 4/1998 | Amirav et al. ................. | 436/154 |
| 6,968,729 B1 * | 11/2005 | Karlsson et al. ............ | 73/23.41 |
| 7,509,837 B2 * | 3/2009 | Lubkowitz et al. .......... | 73/23.35 |
| 2002/0146350 A1 * | 10/2002 | Lo et al. .......................... | 422/89 |
| 2005/0257600 A1 * | 11/2005 | Karlsson et al. ............. | 73/23.41 |
| 2006/0275174 A1 * | 12/2006 | Matsushita et al. ............. | 422/54 |

* cited by examiner

*Primary Examiner* — Lisa Caputo
*Assistant Examiner* — Punam Roy
(74) *Attorney, Agent, or Firm* — John Alumit

(57) ABSTRACT

The invention relates to a field gas chromatograph with flame ionization for the analysis of a gaseous mixture of hydrocarbons, extracted, in particular, from oil drilling mud. Said mixture consists of a fraction of heavy hydrocarbons (beyond pentane) dissolved in mud in gaseous form. Said field gas chromatograph is made up of two independent analysis circuits, dephased by half a cycle and synchronized one with the other. Said analysis circuits are comprised of at least one sampling cell in a preferred design layout, at least one capillary separation chromatography column, at least one flame ionization detector, and at least one electrometer for the conversion of an electrical current, collected by the flame ionization detector, into a voltage signal describing a chromatogram.

13 Claims, 4 Drawing Sheets

| NAME | R.T. | R.T. REF | AREA | AREA REF | PPM |
|---|---|---|---|---|---|
| | 108.58 | UNK | 924.3477 | | |
| | 113.21 | UNK | 455.374 | | |
| HEXANE | 118.17 | 119 | 848.748 | 78.050 | 436 |
| | 120 | UNK | 64.951 | | |
| | 127.20 | UNK | 2.768 | | |
| | 129.55 | UNK | 56.872 | | |
| | 132.06 | UNK | 580.580 | | |
| | 134.25 | UNK | 57.209 | | |
| | 137.50 | UNK | 2.181 | | |
| BENZENE | 144.54 | 145 | 141.151 | 31.448 | 93.3 |
| CYCLOHEXANE | 150.47 | 151.50 | 743.043 | 31.527 | 490.2 |
| | 155.83 | UNK | 392.646 | | |
| EPTANE | 165.19 | UNK | 456.963 | | |
| | 170.95 | 172 | 414.755 | 88.200 | 240.2 |
| | 191.84 | UNK | 45.091 | | |
| METHYLCYCLOHEXANE | 195.35 | 197 | 706.714 | 36.024 | 408 |
| | 199.08 | UNK | 85.521 | | |
| | 203.53 | UNK | 58.129 | | |
| | 210.94 | UNK | 71.631 | | |
| | 218.65 | UNK | 68.400 | | |
| TOLUENE | 227.52 | 229 | 189.360 | 34.197 | 106.3 |
| | 232.11 | UNK | 43.980 | | |
| | 234.98 | UNK | 126.577 | | |

Fig.4

FIELD GAS CHROMATOGRAPH WITH FLAME IONIZATION

CROSS-REFERENCE TO RELATED APPLICATION

This application claims the benefit of the priority filing date in Italian patent application no. MI2010A000183 filed on Feb. 8, 2010.

FEDERALLY SPONSORED RESEARCH

None

SEQUENCE LISTING OR PROGRAM

None

STATEMENT REGARDING COPYRIGHTED MATERIAL

Portions of the disclosure of this patent document contain material that is subject to copyright protection. The copyright owner has no objection to the facsimile reproduction by anyone of the patent document or the patent disclosure as it appears in the Patent and Trademark Office file or records, but otherwise reserves all copyright rights whatsoever.

BACKGROUND

1. Field of the Invention

The present invention relates to a field gas chromatograph with flame ionization for the analysis of a gaseous mixture of hydrocarbons extracted, in particular, from oil drilling mud. The mixture that is the object of analysis is made up of a fraction of heavy hydrocarbons (beyond pentane) dissolved in mud in gaseous form. There are many heavy hydrocarbons, in addition to the pentane, present in mud and dissolved in gaseous form in variable concentrations. Those of particular interest in relation to the present invention are preferably, but not exclusively, hexane, heptane, cyclohexane, methylcyclohexane, benzene and toluene.

2. Background of the Invention

A fraction of light gases from methane to pentane is commonly analysed via the use of various technologies, both in land oil drilling sites and offshore platforms. Only in recent times have services been introduced which offer the analysis of hydrocarbon gases beyond pentane, in oil drilling sites.

At the current state of the art, analysis of the concentration of a fraction of heavy hydrocarbon gaseous dissolved in drilling mud is carried out by gas chromatography coupled with mass spectrometry, or via gas chromatography combined with a detector which measures changes in thermal conductivity (thermal conductivity detector or TCD).

The use of a gas chromatograph-mass spectrometer combination involves the management of two separate instruments, one for the separation of gases over time along a chromatography column (gas chromatograph), the other for quantifying the concentration of a single gas species investigated in the sample of gas (mass spectrometry). The gas line is much more complex and difficult to manage this way. The spectrometer is also a very delicate instrument which is affected by environmental conditions. Its maintenance on site is in fact complex. Moreover, the use of a gas chromatography/mass spectrometry combination is made more complex by the fact that this type of measurement is affected by the presence of environmental gases, such as, among others, oxygen, nitrogen, CO, and $CO_2$. This occurs because the spectrometer is not a selective analyser for hydrocarbons, but is able to detect the presence of any gas which generates ions of mass equal to that for which the analysis was programmed.

Also, in the case of the gas chromatography/TCD analysis combination, there is a problem of noise caused by the environmental gases. Although accurate instruments, TCD sensors are not selective for hydrocarbons. Since they are based on the reading of variations in the thermal conductivity of the gas analysed, TCD sensors in fact reveal the presence of all the gases in the sample, both hydrocarbons and environmental gases, or those from the drilling mud. Moreover, it is not possible to measure the sum of the hydrocarbons as a whole with the same type of TCD sensor with which the single hydrocarbons are analysed. Consequently, during analysis of the data, it is not possible to carry out a quality check by comparing the sum of the single hydrocarbon gaseous species and the analysis commonly known as total gas (total hydrocarbons).

The object of the present invention is, therefore, to provide an instrument which is able to analyse a gaseous mixture of hydrocarbons extracted, in particular, from oil drilling mud, and quantify a heavy fraction of gas thereof with accurate and precise measurements; while at the same time, provide an instrument that is easy to manage in remote land oil drilling sites and offshore platforms, even in difficult environmental conditions.

A second object of the present invention is to provide an instrument which is able to analyse a gaseous mixture of hydrocarbons extracted, in particular, from oil drilling mud, and quantify a heavy fraction of the gas present; while at the same time, provide an instrument that is able to perform a precise analysis in a continuous manner.

Another object of the present invention is to provide an instrument for the analysis of a gaseous mixture of hydrocarbons extracted, in particular, from oil drilling mud, and quantify a heavy gas fraction thereof; while at the same time, provide an instrument that is able to respond linearly both in the presence of concentrations of a few parts per million (ppm) and in the presence of a very high concentration of hydrocarbons in the gaseous mixture.

SUMMARY OF THE INVENTION

These and other objects of the present invention are achieved by means of a gas chromatograph made up of two independent and synchronised analysis circuits, whose parts are each designed so as to optimise both the efficiency of each individual mechanical component and the analysis process seen as a whole.

Each individual circuit comprises a single capillary column through which components of hydrocarbons of different molecular weight (present in a gaseous mixture) flow at different rates according to how they interact with an internal silicone film of the capillary column, and through which said components exit at the end of the column at different times.

The concentration of single components is measured by means of a flame ionization detector, or FID, placed downstream of the capillary column.

An electrometer converts the electrical current from the FID into a voltage signal which produces a chromatogram formed by the same number of peaks as the components of hydrocarbons separated; the area subtended to each peak being proportional to the concentration of the relative hydrocarbon component. Among all the peaks identified and generated by the different hydrocarbons present in gaseous form in the sample analysed, those relative to the gases investigated are recognised on the basis of their retention time, which is calibrated previously with a mixture of known composition.

While drilling for hydrocarbons, it is then possible to correlate the chromatographic analysis with the depths of drilling from which the gas analysed has been released.

The choice of flame ionization sensor allows an analysis of only the combustible gas fraction, and thus only the hydrocarbon fraction; unlike what occurs with the sensors described above, such as the mass spectrometer and TCD.

As part of the site analysis, flame ionization chromatographs are, to date, commonly used for the analysis of gaseous mixtures up to only pentane. In particular, an Italian patent filed the Applicant (Assignee, GEOLOG S.p.A.) [No. MI2001A001329] describes the manufacture of a FID chromatograph based on a double analysis circuit for the analysis of a gaseous mixture of hydrocarbons extracted, in particular, from oil drilling mud in conditions of offshore drilling platforms or land sites. The instrument described by said patent and currently used in widespread manner is marketed under the registered trademark DualFID®. The instrument DualFID® is able to perform an analysis of light hydrocarbons (up to pentane). In order to also analyse heavy hydrocarbons (beyond pentane), numerous, in-depth research projects have been performed which have led to the manufacture of the instrument which is the object of the present invention. The latter, unlike the DualFID® instrument and the other flame ionization chromatographs on the market, provides for the use of a flame ionization chromatograph for the analysis of a fraction of heavy hydrocarbon gases beyond pentane, in remote land oil drilling sites and offshore platforms. Said gases are, preferably but not exclusively, hexane, heptane, cyclohexane, methylcyclohexane, benzene and toluene.

In addition to what is described above, the instrument proposed in the present invention, although providing for the presence of two analysis circuits, differs from the instrument marketed under the trademark DualFID®, both from a technical construction point of view and in the methods of analysis.

The double analysis circuit of DualFID® consists of a first analysis unit comprising a first separation assembly with chromatography columns connected to a respective first flame ionization device for chromatographic analysis of methane and ethane components of a gaseous mixture, and a second analysis unit functioning simultaneously and in parallel to the first analysis unit. Said second analysis unit comprises a second separation assembly with chromatography columns connected to a respective second flame ionization device for the chromatographic analysis of other components of hydrocarbons under investigation, i.e. propane and pentane. The instrument that is the object of this patent application provides, instead, for a double analysis circuit in order to cut the analysis frequency in half. The two circuits do not work in parallel as in DualFID®, but are instead dephased by half a cycle. In the present invention, the two analysis circuits are identical and both analyse the same fraction of heavy hydrocarbons (beyond pentane) dissolved in mud in gaseous form. Said hydrocarbons are, preferably but not exclusively, hexane, heptane, cyclohexane, methylcyclohexane, benzene and toluene.

These and other features will be explained in greater detail by the following description of the present invention.

The use of a flame ionization gas chromatograph for the analysis of a heavy fraction of hydrocarbon gases dissolved in drilling mud allows two fundamental objectives to be achieved: 1) high precision and repeatability in the analysis; 2) easy management and maintenance of the instrument.

The gas chromatograph of the present invention is therefore made up of two internal analysis circuits, independent and synchronised via software, one in respect of the other. Each circuit is made up of:

- rotary sampling micro valves with micro volumes for capillary chromatography, appropriately designed to ensure performances of high sensitivity;
- an Apolar capillary column of such length as to guarantee an optimal separation of the peaks;
- a system for back-purging of the capillary column, in order to guarantee that after every analysis there is no trace left in the chromatography column of the gas analysed'
- a FID analyser with micro volumes specifically for capillary columns;
- carrier gas inside the capillary column;
- a heat-regulated electronic regulator to maintain a constant flow rate of the carrier gas;
- a zero air generator for the generation of air required by a FID; The choice of the zero generator enables background noise to be reduced to a minimum; and
- a suction pump or ejector placed at the vent of the chromatograph for the aspiration of gas from a gas line. Unlike instruments for the analysis of light gases (from methane to pentane), the system of analysis of heavy gases that forms the object of this patent is not connected to the system of distribution of the standard gas already present in a cab, positioned upstream of the instrument. This enables the entire gas line to be maintained in a vacuum so as to avoid condensation of heavier gaseous fractions and prevent gas from passing through any diaphragm before analysis, thus avoiding the phenomena of adsorption of the heavy gases.

These and other aspects will be explained in greater detail by the following description of a preferred embodiment of the present invention, to be read by way of a non-limiting exam of the more general principle claimed.

BRIEF DESCRIPTION OF THE DRAWINGS

The following description refers to the accompanying drawings, in which:

FIG. 4 shows a table of the output from the instrument together with the chromatogram shown in FIG. 3.

DESCRIPTION OF PREFERRED EMBODIMENTS

Figure 1:
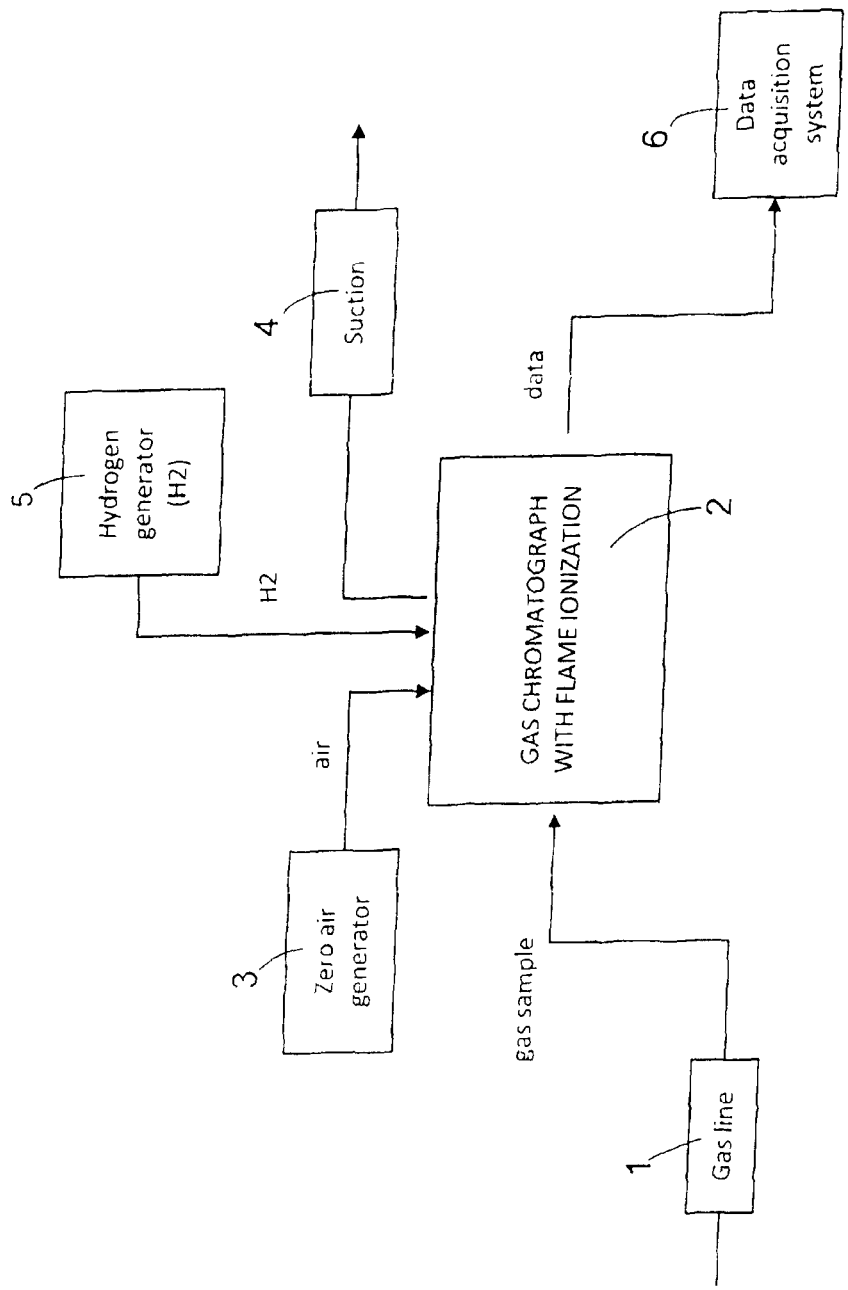
FIG. 1 is an example diagram of the functioning of the system as a whole in flow diagram terms.

Referring to FIG. 1, the gas extracted from a degasser (not shown in the drawing) is transported towards a cab via a gas line (1).

The degasser is preferably a degasser able to treat a constant volume of mud. Upstream of the degasser, a heater of drilling mud can be provided in the event mud comes to the surface at particularly low temperatures, which would prevent or reduce the efficacy of degassing. This occurs above all on drilling platforms where the water column is such that the mud has time to cool considerably.

The gas line (1) is made preferably of Teflon in order to avoid the phenomena of adsorption and to avoid delay in transit times for various heavy gases. The gas line (1) is preferably heated, or at least insulated thermally in respect of the outside, so as to maintain such a temperature as to reduce the possibility of the effects of condensation of heavy gases along the same line.

For both analysis circuits, the gas is sampled upon input to the chromatograph (2) from the gas line by means of a rotary micro valve specifically for capillary chromatography. The valve guarantees constant and repeatable sampling of a small sample amount, reducing dead volumes to a minimum inside the same valve. The sampling valve is connected to a capillary column through which components of hydrocarbons of various molecular structures and weight from the gaseous mixture flow at different rates according to their affinity with the chromatographic material contained in the same column. The components then exit at the end of the capillary column separated one from the other. The capillary column was chosen after strict laboratory tests so as to be able to optimally separate the peaks of the six gas species being analysed. The capillary column chosen for this application is characterised by an internal phase of the apolar type and is 50 m long.

The air necessary as comburent for the flame ionization detector is supplied by a zero air generator (3), and thus free from impurity. In this way, the background noise is rendered virtually null, and therefore, a flame ionization gas chromatograph is obtained which is able to identify compounds present in gaseous mixture in concentrations equal to a few parts per million (ppm).

Unlike instruments for the analysis of light gases (from methane to pentane), aspiration of gas is applied downstream of the chromatograph (4), preferably via an ejector, or alternatively, by means of a suction pump. Application of aspiration downstream of the instrument provides a dual advantage: a) the gas line is maintained in a vacuum along its whole extension so as to further reduce the possibility of condensation of heavy gases;
b) the gas does not pass through the suction pump before the analysis instrument; in this way, the possible phenomena of adsorption on the diaphragm of the same pump is avoided.

The concentration of single components is measured by means of a flame ionization detector, or FID, placed downstream of the capillary column. The carrier gas used, coming from a special generator (5), is preferably hydrogen (H2) which, owing to its low molecular weight in relation to air, allows for a greater efficiency of separation of the components of hydrocarbons through the capillary column.

An electrometer converts the electrical current coming from the FID into a voltage signal which produces a chromatogram formed by the same number of peaks as the components of hydrocarbons separated; the area subtended to each peak being proportional to the concentration of the relative hydrocarbon component. Among all the peaks identified, i.e., generated by the different hydrocarbons present in gaseous form, those relative to the gases investigated are recognised on the basis of their retention time calibrated previously with a mixture of known composition. The concentration values measured in this way are then transmitted to a data acquisition system (6) present in an operative unit where the instrument is installed. The data can be transmitted either through a serial port or through a network. The chromatogram relating to the analysis and the relative concentration data can likewise be transmitted to a printer, preferably via a USB port, in real time. A certain number of analyses, preferably numbering 100, are kept in computer memory present in the chromatograph itself, which can be easily called up and sent for printing at a later time.

The preferred embodiment of the gas chromatograph provides for two analysis circuits whose cycle has a duration preferably equal to 240 seconds. The two circuits are equal in every single part, and work dephased by half a cycle in such a way as to sample the gas from the same gas line alternatively every 120 seconds. This allows as a result, in terms of the concentration of gas species detected, to be available every 120 seconds. Their functioning will be described in detail herein below. The possibility is not, however, excluded of alternative embodiments aimed at the optimisation of the times of analysis and of resolution of the chromatographic peaks.

The gas chromatograph which is the object of this patent allows prior tests and calibrations to be carried out by injection of gas samples from the front panel. This system is managed by mini solenoid valves with diaphrams preferably made in Kalrez®. The choice of said material was made because polymer does not result in the phenomena of heavy gas adsorptions, however, other equivalent solutions are also possible in order to achieve the same results.

In the preferred embodiment, each circuit is composed of a 40 µl sampling loop. Rotary sampling micro valves with micro volumes for capillary chromatography are used in order to ensure repeatable and constant values even in the case of a few microlitres of gaseous mixture. The internal volumes of said valves are optimised for capillary chromatography so as to reduce dead spaces in the analysis cycle to a minimum. The material with which the gas comes into contact is Teflon with a glass filler (Rulon®). Said material does not result in the phenomena of adsorption of the heavier molecules of the gaseous mixture on the valve itself. The length and type of capillary column chosen are specific for obtaining optimal separation of all the peaks relating to the gas species under investigation. After various laboratory tests, a capillary column of the apolar type, 50 m long, was chosen. The mixture of sampled gas flows through a capillary column, which is maintained at a constant temperature inside a heating chamber, also known as an oven.

Separation efficiency of hydrocarbon components of various molecular weight is optimised using hydrogen (H2), instead of air, as the carrier gas for mixture through the chromatography column. In the preferred embodiment, the flow of the carrier gas is constantly maintained throughout the analysis cycle. The gas chromatograph is provided internally with a heat-regulated electronic regulator to maintain the pressure of the carrier constant.

Nevertheless, use of a variable flow is not excluded in cases where it is found to be advantageous for the purposes of the analysis. For this reason, in the manufacture of the instrument which is the object of the patent, it is possible to program two ramps of carrier gas pressure with an electronic control.

The capacity for precisely distinguishing chromatographic peaks of all hydrocarbon components of a gaseous mixture, irrespective of the concentrations with which they are presented in the mixture; the high efficiency of separation between hydrocarbon components of a gaseous mixture by a 50 m apolar capillary column chosen for the preferred embodiment; and the possibility of sampling such a reduced, yet constant and repeatable, volume of a gaseous mixture; all contribute to obtaining a linear response of the apparatus to the various concentrations of hydrocarbon components in a gaseous mixture, and without the occurrence of the phenomena of saturation in the case of extremely high concentrations of hydrocarbon components in a gaseous mixture.

The gas chromatograph, in its preferred embodiment, is made up of two independent and synchronised analysis circuits which are dephased by half a cycle.

Figure 2:
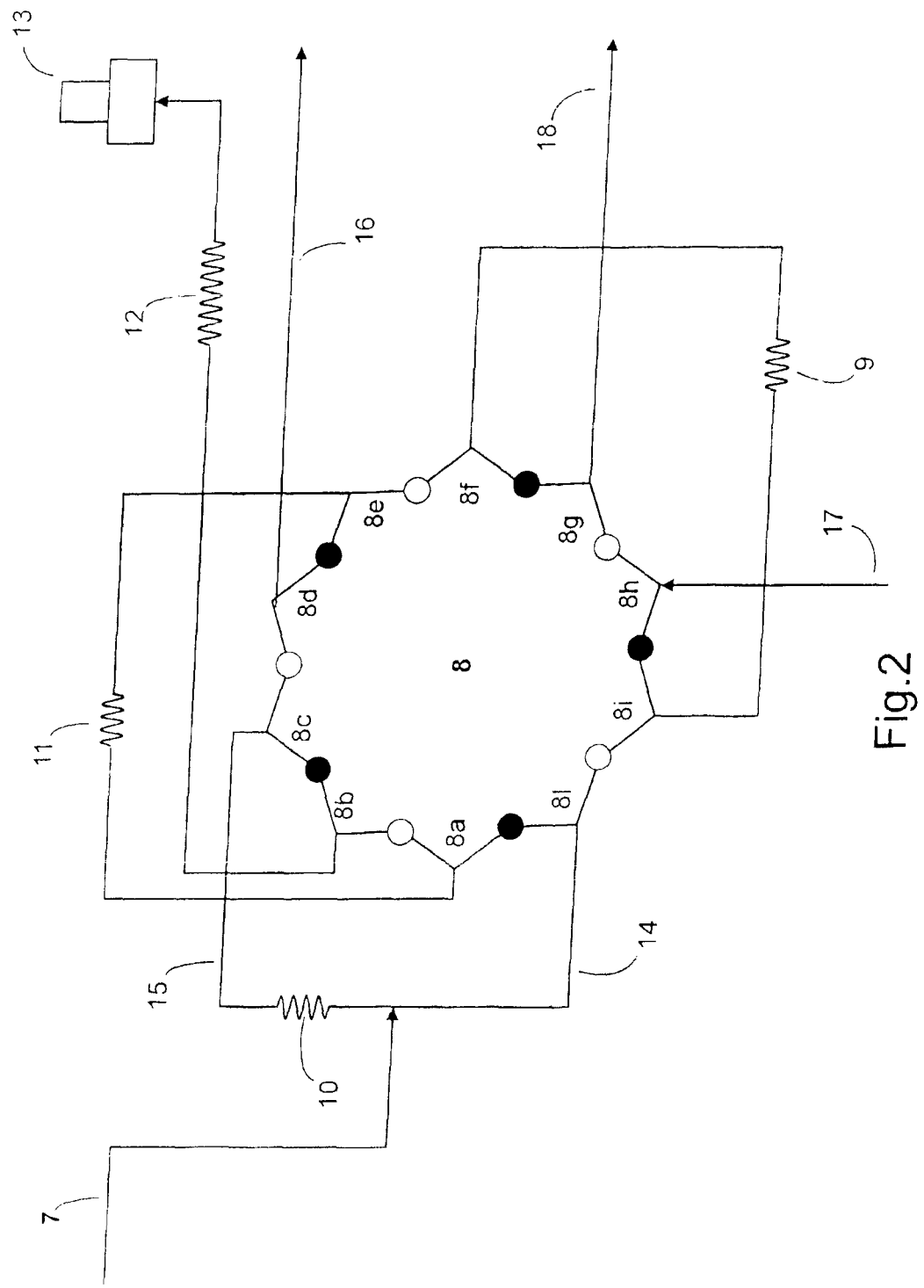
FIG. 2 is a simplified representation of the internal diagram of the chromatograph for a single circuit.

FIG. 2 provides a detailed description of a single analysis circuit, taking into account the fact that the two circuits, in the preferred embodiment, are identical.

Each analysis circuit is composed of a carrier gas supply line (7); a ten-way rotary valve with micro volumes (sampling valve) (8); a sampling cell (sample loop) (9); a purging column (10) and a symmetrical column of compensation (11); an apolar capillary column 50 m long (12); a flame ionization detector FID (13) directly connected to the capillary chromatography column and an electrometer (not shown) which converts a current collected by the FID into a voltage signal which generates a chromatogram.

It should be noted that the purging column (10) and the compensation column (11) have identical structural features so as to guarantee that the carrier gas undergoes the same load losses and the circuit stays balanced.

The sampling valve is of a rotary type with ten ways and can be switched between two working conditions corresponding to two separate phases of the analysis cycle of the double analysis circuit. In the first switching state, the ways (8a) and (8b), (8c) and (8d), (8e) and (8f), (8g) and (8h), (8i) and (8l) are in communication in pairs, while in the second working condition, the ways (8b) and (8c), (8d) and (8e), (8f) and (8g), (8h) and (8i), (8l) and (8a) are in communication in pairs.

The circuit supplying the carrier gas (7) to the sampling valve (8) has an inlet for the supply of the carrier gas and ends with a node from which a first (14) and a second branch (15) lead off. The first branch (14) of the circuit supplying the carrier gas is connected to the way (8l) of the sampling valve (8). The second branch (15) of the circuit supplying the carrier gas is connected to the way (8c) of the sampling valve (8) and constitutes the purging column (10).

A connection between the way (8a) and the way (8e) of the sampling valve (8) constitutes a first compensation column (11). A connection between the way (8f) and the way (8i) of the sampling valve constitutes a sampling cell (9), also known as a sample loop.

The sampling valve (8) is then directly connected to the flame ionization detector (FID) (13) via the capillary column of separation (12).

A conduit (16) connects the way (8d) of the sampling valve (8) to the outlet of the purging and compensation columns.

The sample of gas to be analysed enters the circuit at the way (8h) of the sampling valve (8) through a conduit (17). A conduit (18) then leads off from the way (8g) to connect the sampling valve (8) to the outlet of the sample.

The first phase of the analysis cycle, known as sampling, is associated with the state of switching of the sampling valve (8) wherein the ways (8a) and (8b), (8c) and (8d), (8e) and (8f), (8g) and (8h), (8i) and (8l) are in communication with each other.

Starting from a condition wherein the sample of gaseous mixture to be analysed has already filled the sampling cell (9), in the first phase of the analysis cycle, part of the flow of hydrogen coming from the first supply branch traverses the branch (14) in succession, enters the sampling valve (8) at the way (81) and exits the way (81), takes the volume of sample from the sampling cell (9), passes from the way (8f) and (8e) and traverses the chromatography column, known as compensation column (11), where the differentiation begins between the various hydrocarbon components on the basis of gas molecule interaction with the internal phase of the capillary column. From the compensation column (11), and through the ways (8a) and (8b) of the valve (8), the sample is finally conveyed towards the separation capillary column (12) as it is rightfully known.

The carrier gas of the second branch (15) in this phase washes the purging column (10) and, through the ways (8c) and (8d), is expelled at the so-called, "vent of the purge" (16).

During this first phase, the sample from the external line (17) is not introduced into the sampling cell, but enters the way (8h) of the sampling valve (8) and exits the way (8g), and conveyed towards the outlet line (18).

This first switching of the sampling valve (8) is maintained for a preset time. Said time was determined by laboratory tests and experiments and is equal to 25 sec. The solution defined is preferable, but other solutions are possible, as long as they are within the scope of the present patent application. After this time, the switching is reversed in order to remove all the hydrocarbons present in the gaseous mixture, which would exit after the last of the gases under investigation.

The second phase of the analysis cycle, known as analysis/counterflow bleeding, originates at the switching of the sampling valve (8) which now places the ways (8b) and (8c), (8d) and (8e), (8f) and (8g), (8h) and (8i), (8l) and (8a) in communication.

During the second phase of the analysis cycle, the sample to be analysed is transported by the carrier gas from the branch (15) through the capillary column (12) and then to the FID (13) where the analysis takes place.

At the same time, another part of the carrier gas, coming from the line (14), and through the ways (8l) and (8a), flows in an opposite direction in relation to the first phase along the compensation column (11) in order to perform back purging; thus eliminating the hydrocarbon components that have accumulated therein at the end of the first phase of the analysis cycle. Afterwards, it goes to the outlet via the line (16) passing via the ways (8e) and (8d).

During this second phase, the sample of gas to be analysed (17) enters the way (8h), passes through the way (8i), and again flows through the sampling cell (9) from which it flows, via the ways (8f) and (8g), towards the outlet of the sample (18).

Figure 3:
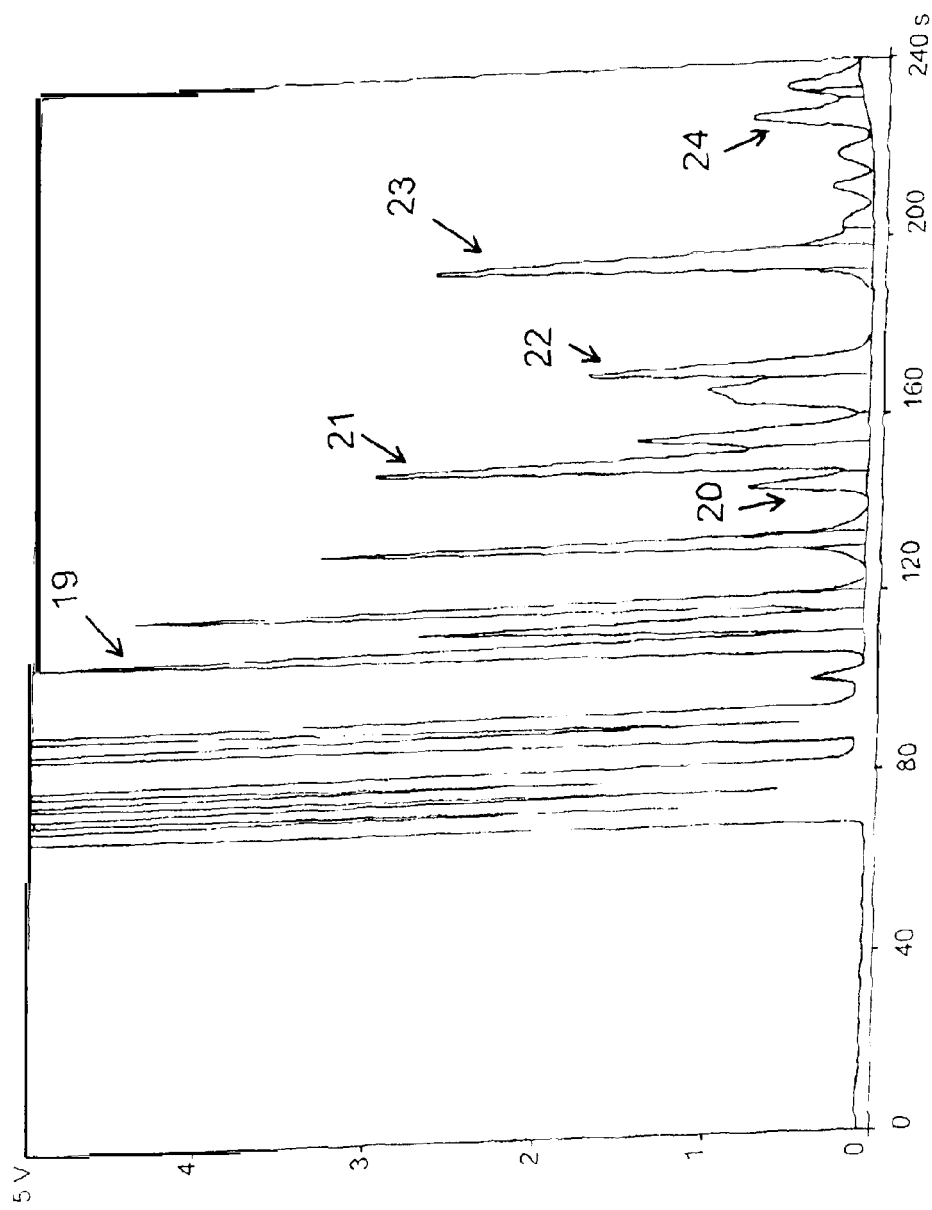
FIG. 3 represents the chromatogram resulting from the analysis performed with a single analysis circuit on a real gas sample coming from drilling mud.

FIG. 3 shows the chromatogram resulting from a single analysis cycle. The analysis cycle relating to the chromatogram in the drawing has a duration of 240 sec, and the instant set by the user as the start of the integration of peaks detected is equal to 100 sec. Starting from said instant, 23 peaks can be recognised which correspond to 23 different hydrocarbon compounds. Of these 23 hydrocarbons, only six are investigated in the preferred embodiment to which FIG. 3 refers. Said peaks are recognised by a software which manages the analysis on the basis of their retention times and are: no. 19 hexane; no. 20 benzene; no. 21 cyclohexane; no. 22 heptane; no. 23 cyclohexane; no. 24 toluene.

FIG. 4 shows a table which an instrument processes together with the chromatogram. In said table, for each peak identified, the retention time (R.T.) and the integrated area (AREA), as well as the reference retention time (R.T. REF) and the reference area (AREA REF) are given. For the peaks investigated specifically on the basis of the calibration, the area is converted into concentration (ppm).

In addition to the preferred embodiment described above, alternative embodiments are not excluded wherein the architecture of the analysis circuits can vary, also comprising several chromatography columns with different features.

A possible first alternative embodiment can, for example, be constituted by an analysis circuit made up of two chromatography columns with different features which work in parallel or in sequence to improve the resolution of the peaks.

A second alternative may be constituted by a duplication of the circuit of the first alternative so as to increase the number of analyses in a unit of time. According to what is described above, the present invention provides an instrument which, optimised in all its parts, guarantees accuracy, precision, compactness and easy management in remote locations of an

What is claimed is:

1. A field gas chromatograph, comprising:
   flame ionization which analyses the heavy fraction of a gaseous mixture of hydrocarbons, including hexane, heptanes, cyclohexane, methylcyclohexane, benzene and toluene, from oil drilling mud and sampled by a transport gas;
   wherein the field gas chromatograph with flame ionization is made up of two half-cycle, de-phased and independent analysis circuits; and
   wherein each of said analysis circuits comprises at least one sampling cell, at least one capillary separation chromatography column, at least one flame ionization detector, and at least one electrometer for the conversion of an electrical current collected by the flame ionization detector into a voltage signal describing a chromatogram.

2. The field gas chromatograph of claim 1, further comprising two analysis circuits synchronized to supply a reading of the concentration of hydrocarbons every 120 seconds.

3. The field gas chromatograph of claim 1, wherein said at least one chromatography column is identical for both circuits.

4. The field gas chromatograph of claim 1, further comprising an aspiration instrument along a gas line applied to a vent of the chromatograph, so as to avoid the passage of a sample through other membranes before entry in the same chromatograph.

5. The field gas chromatograph of claim 4, wherein the sample is taken from a gas line maintained in vacuum condition so as to reduce the risk of condensation of heavy gases along any point of the same line by means of aspiration applied to the vent of the chromatograph.

6. The field gas chromatograph of claim 1, wherein air used by the flame ionization detector for combustion is supplied by a zero air generator so as to reduce background noise of the sample to a minimum.

7. The field gas chromatograph of claim 1, wherein the transport gas is hydrogen.

8. The field gas chromatograph of claim 1, wherein the field gas chromatograph comprises at least one heat-regulated electronic regulator inside said gas chromatograph in order to maintain a constant flow rate of the transport gas.

9. The field gas chromatograph of claim 1, wherein the field gas chromatograph manages two pressure ramps for the transport of gas by way of electronic control.

10. The field gas chromatograph of claim 1, wherein the field gas chromatograph provides for the use of sampling valves for capillary chromatography.

11. The field gas chromatograph of claim 1, wherein the field gas chromatograph comprises a front panel and provides for performing calibrations and tests by injecting gas samples from the front panel by means of a system managed by mini solenoid valves.

12. The field gas chromatograph of claim 1, wherein the field gas chromatograph comprises a first phase referred to as a phase of sampling and circulation of the gas through the chromatograph column up to the flame ionization detector, and a second phase of analysis and counter-flow bleeding wherein the transport gas scrubs the chromatograph columns in counter flow.

13. The field gas chromatograph with flame ionization according to claim 1, wherein, said chromatograph columns are different according to the circuit.

* * * * *